(12) United States Patent
Azarnia

(10) Patent No.: US 9,005,671 B2
(45) Date of Patent: *Apr. 14, 2015

(54) CONCENTRATED AQUEOUS BROMINE SOLUTIONS AND THEIR PREPARATION

(75) Inventor: Farah D. Azarnia, Baton Rouge, LA (US)

(73) Assignee: Albemarle Corporation, Richmond, VA (US)

( * ) Notice: Subject to any disclaimer, the term of this patent is extended or adjusted under 35 U.S.C. 154(b) by 1739 days.

This patent is subject to a terminal disclaimer.

(21) Appl. No.: 11/574,592

(22) PCT Filed: Sep. 7, 2005

(86) PCT No.: PCT/US2005/032239
§ 371 (c)(1),
(2), (4) Date: Oct. 28, 2008

(87) PCT Pub. No.: WO2006/029354
PCT Pub. Date: Mar. 16, 2006

(65) Prior Publication Data
US 2009/0053327 A1 Feb. 26, 2009

Related U.S. Application Data

(60) Provisional application No. 60/607,293, filed on Sep. 7, 2004.

(51) Int. Cl.
*A01N 59/00* (2006.01)
*A01P 1/00* (2006.01)
*A01N 39/00* (2006.01)
(Continued)

(52) U.S. Cl.
CPC . *C02F 1/76* (2013.01); *A01N 59/00* (2013.01); *C02F 1/50* (2013.01); *C02F 1/766* (2013.01)

(58) Field of Classification Search
USPC ............... 424/663, 703, 615, 665, 680, 723
See application file for complete search history.

(56) References Cited

U.S. PATENT DOCUMENTS 3,152,073 A 10/1964 Morton
3,170,883 A 2/1965 Owen et al.
(Continued)

FOREIGN PATENT DOCUMENTS

EP 1080641 A3 3/2001
EP 1411995 B1 5/2009
(Continued)

OTHER PUBLICATIONS

Clare, A..S., "Marine Natural Product Antifoulants: Status and Potential," Biofouling (1996) 9: 211-229.
(Continued)

*Primary Examiner* — Ernst V Arnold
*Assistant Examiner* — Hong Yu
(74) *Attorney, Agent, or Firm* — Marcy M. Hoefling

(57) ABSTRACT

This invention provides concentrated aqueous biocidal solutions formed from bromine chloride, sodium hydroxide, and sulfamic acid. The weight ratio of bromine chloride:sodium hydroxide:sulfamic acid used in forming the concentrated solution is such that for every 10.5 to 11.5 parts by weight of bromine chloride used, 15.3 to 17.5 parts by weight of sodium hydroxide and 11.0 to 12.5 parts by weight of sulfamic acid are used, the biocidal solution containing at least about 100,000 ppm (wt/wt) of active bromine based on the total weight of the solution.

31 Claims, 2 Drawing Sheets

Thermal Stability at 130° F

(51) Int. Cl.
*A01N 59/02* (2006.01)
*A01N 59/08* (2006.01)
*C02F 1/76* (2006.01)
*C02F 1/50* (2006.01)

(56) References Cited

U.S. PATENT DOCUMENTS

| | | | |
|---|---|---|---|
| 3,222,276 | A | 12/1965 | Belohlav et al. |
| 3,308,062 | A | 3/1967 | Gunther |
| 3,328,294 | A | 6/1967 | Self et al. |
| 3,558,503 | A | 1/1971 | Goodenough et al. |
| 3,589,859 | A | 6/1971 | Foroulis |
| 3,711,246 | A | 1/1973 | Foroulis |
| 3,749,672 | A | 7/1973 | Golton et al. |
| 3,767,586 | A | 10/1973 | Rutkiewic |
| 4,032,460 | A | 6/1977 | Zilch et al. |
| 4,237,090 | A | 12/1980 | DeMonbrun et al. |
| 4,295,932 | A | 10/1981 | Pocius |
| 4,382,799 | A | 5/1983 | Davis et al. |
| 4,427,435 | A | 1/1984 | Lorenz et al. |
| 4,451,376 | A | 5/1984 | Sharp |
| 4,465,598 | A | 8/1984 | Darlington et al. |
| 4,476,930 | A | 10/1984 | Watanabe |
| 4,490,308 | A | 12/1984 | Fong et al. |
| 4,539,071 | A | 9/1985 | Clifford et al. |
| 4,546,156 | A | 10/1985 | Fong et al. |
| 4,566,973 | A | 1/1986 | Masler, III et al. |
| 4,595,517 | A | 6/1986 | Abadi |
| 4,595,691 | A | 6/1986 | LaMarre et al. |
| 4,604,431 | A | 8/1986 | Fong et al. |
| 4,642,194 | A | 2/1987 | Johnson |
| 4,643,835 | A | 2/1987 | Koeplin-Gall et al. |
| 4,661,503 | A | 4/1987 | Martin et al. |
| 4,680,339 | A | 7/1987 | Fong |
| 4,680,399 | A | 7/1987 | Buchardt |
| 4,703,092 | A | 10/1987 | Fong |
| 4,711,724 | A | 12/1987 | Johnson |
| 4,752,443 | A | 6/1988 | Hoots et al. |
| 4,759,852 | A | 7/1988 | Trulear |
| 4,762,894 | A | 8/1988 | Fong et al. |
| 4,777,219 | A | 10/1988 | Fong |
| 4,801,388 | A | 1/1989 | Fong et al. |
| 4,802,990 | A | 2/1989 | Inskeep, Jr. |
| 4,822,513 | A | 4/1989 | Corby |
| 4,846,979 | A | 7/1989 | Hamilton |
| 4,883,600 | A | 11/1989 | MacDonald et al. |
| 4,886,915 | A | 12/1989 | Favstritsky |
| 4,898,686 | A | 2/1990 | Johnson et al. |
| 4,906,651 | A | 3/1990 | Hsu |
| 4,923,634 | A | 5/1990 | Hoots et al. |
| 4,929,424 | A | 5/1990 | Meier et al. |
| 4,929,425 | A | 5/1990 | Hoots et al. |
| 4,966,716 | A | 10/1990 | Favstritsky et al. |
| 4,992,209 | A | 2/1991 | Smyk et al. |
| 4,995,987 | A | 2/1991 | Whitekettle et al. |
| 5,034,155 | A | 7/1991 | Soeder et al. |
| 5,035,806 | A | 7/1991 | Fong et al. |
| 5,047,164 | A | 9/1991 | Corby |
| 5,055,285 | A | 10/1991 | Duncan et al. |
| 5,118,426 | A | 6/1992 | Duncan et al. |
| 5,120,452 | A | 6/1992 | Ness et al. |
| 5,120,797 | A | 6/1992 | Fong et al. |
| 5,141,652 | A | 8/1992 | Moore, Jr. et al. |
| 5,179,173 | A | 1/1993 | Fong et al. |
| 5,192,459 | A | 3/1993 | Tell et al. |
| 5,194,238 | A | 3/1993 | Duncan et al. |
| 5,196,126 | A | 3/1993 | O'Dowd |
| 5,202,047 | A | 4/1993 | Corby |
| 5,259,985 | A | 11/1993 | Nakanishi et al. |
| 5,264,136 | A | 11/1993 | Howarth et al. |
| 5,389,384 | A | 2/1995 | Jooste |
| 5,414,652 | A | 5/1995 | Mieda et al. |
| 5,424,032 | A | 6/1995 | Christensen et al. |
| 5,443,849 | A | 8/1995 | Corby |
| 5,464,636 | A | 11/1995 | Hight et al. |
| 5,525,241 | A | 6/1996 | Clavin et al. |
| 5,527,547 | A | 6/1996 | Hight et al. |
| 5,589,106 | A | 12/1996 | Shim et al. |
| 5,607,619 | A | 3/1997 | Dadgar et al. |
| 5,679,239 | A | 10/1997 | Blum et al. |
| 5,683,654 | A | 11/1997 | Dallmier et al. |
| 5,795,487 | A | 8/1998 | Dallmier et al. |
| 5,900,512 | A | 5/1999 | Elnagar et al. |
| 5,922,745 | A | 7/1999 | McCarthy et al. |
| 5,942,126 | A | 8/1999 | Dallmier et al. |
| 6,007,726 | A | 12/1999 | Yang et al. |
| 6,015,782 | A | 1/2000 | Petri et al. |
| 6,037,318 | A | 3/2000 | Na et al. |
| 6,068,861 | A | 5/2000 | Moore, Jr. et al. |
| 6,110,387 | A | 8/2000 | Choudhury et al. |
| 6,123,870 | A | 9/2000 | Yang et al. |
| 6,156,229 | A | 12/2000 | Yang et al. |
| 6,270,722 | B1 | 8/2001 | Yang et al. |
| 6,287,473 | B1 | 9/2001 | Yang et al. |
| 6,322,822 | B1 * | 11/2001 | Moore et al. .................. 424/703 |
| 6,423,267 | B1 | 7/2002 | Yang et al. |
| 2006/0278586 | A1 * | 12/2006 | Nalepa et al. ................. 210/754 |

FOREIGN PATENT DOCUMENTS

| | | |
|---|---|---|
| WO | 90/15780 A1 | 12/1990 |
| WO | 96/14092 A1 | 5/1996 |
| WO | 96/30562 A1 | 10/1996 |
| WO | 97/20546 A1 | 6/1997 |
| WO | 97/20909 A1 | 6/1997 |
| WO | 97/34827 A1 | 9/1997 |
| WO | 97/43392 A1 | 11/1997 |
| WO | 98/15609 A1 | 4/1998 |
| WO | 99/06320 A1 | 2/1999 |
| WO | 99/32596 A1 | 7/1999 |
| WO | 99/55627 A1 | 11/1999 |
| WO | 00/34186 A1 | 6/2000 |

OTHER PUBLICATIONS

S. Tsukamoto, et al., "Ceratinamides A and B: New Antifouling Dibromotyrosine Derivatives from the Marine Sponge *Pseudoceratina purpurea*," Tetrahedron (1996) 52: 8181-8186.

W. Miki, K. Kon-ya, and S. Mizobuchi, "Biofouling and Marine Biotechnology: New Antifoulants from Marine Invertebrates," Journal of Marine Biotechnology (1996) 4: 117-120.

H. Genthe, "The Incredible Sponge," Smithsonian (Aug. 1998) 29: 50-54, 56, and 58.

M. Givskov, et al., "Eukaryotic Interference with Homoserine Lactone-Mediated Prokaryotic Signaling," Journal of Bacteriology (1996) 178: 6618-6622.

D. Ren, J.J. Sims, and T.K. Wood, "Inhibition of Biofilm Formation and Swarming of *Bacillus subtilus* by (5Z)-4-Bromo-5-(Bromomethylene)-3-Butyl-2(5H)-Furanone," Letters in Applied Microbiology (2002) 34: 293-299.

M.E. Weeks, "Discovery of the Elements: XVII. The Halogen Family," Journal of Chemical Education (1932) 9: 1915-1939.

A.J. Balard, Annales de Chemie et de Physique (1826), vol. 32, pp. 371-372.

H.S. Rzepa, "Elemental and Molecular Heritage: An Internet-Based Display," Molecules (1998) 3: 4 pages.

B. Grinbaum and M. Friedman, "Bromine," in Kirk-Othmer Encyclopedia of Chemical Technology 4th Ed. (New York, NY: John Wiley and Sons, Inc., 2001), vol. 4, pp. 548-549.

F. Yaron, "Bromine Manufacture: Technology and Economic Aspects," in "Bromine and Its Compounds," Z.E. Jolles, ed., pp. 3-11 and 41 (New York, NY: Academic Press, 1966).

"Bromine Brine," Arkansas Geological Commission, web address www.state.ar.us/agc/bromine.htm; 1 page, website visited Sep. 26, 2003.

R.D. Bartholomew, "Bromine-based Biocides for Cooling Water Systems: A Literature Review," Paper IWC 98-74 (Pittsburgh, PA: Engineers' Society of Western Pennsylvania, 1998), 30 pgs.

F.W. Tanner and G. Pitner, "Germicidal Action of Bromine," Proceedings of the Society for Experimental Biology and Medicine (1939) 40: 143-145.

(56) References Cited

OTHER PUBLICATIONS

T.D. Beckwith and J.R. Moser, "Germicidal Effectiveness of Chlorine, Bromine and Iodine"; Journal of the American Water Works Association (1933) 25: 367-374.

D.R. Wood and E.T. Illing, "The Sterilisation of Sea Water by Means of Chlorine"; The Analyst 1930, vol. 55: pp. 125-126.

J. A. McCarthy, "Bromine and Chlorine Dioxide as Water Disinfectants"; Journal of the New England Water Works Association (1944) 58: 55-68.

O. Wyss and R.J. Stockton, "The Germicidal Action of Bromine," Arch. Biochem. (1947) 12:267-271.

E.A. Shilov and J.N. Gladtchikova, "On the Calculation of the Dissociation Constants of Hypohalogenous Acids from Kinetic Data," Journal of the American Chemical Society (1938) 60: 490-491.

G.M. Fair, et al., "The Behavior of Chlorine as a Water Disinfectant," Journal of the American Water Works Association (1948) 40: 1051-1061.

E.K. Rideal and U.R. Evans, "The Effect of Alkalinity on the Use of Hypochlorites," Journal of the Society of the Chemical Industry (1921) 40: 64R-66R.

C.K. Johns, "Germicidal Power of Sodium Hypochlorite," Industrial and Engineering Chemistry (1934) 26: 787-788.

G.R. Dychala, "Chlorine and Chlorine Compounds" in Disinfection, Sterilization, and Preservation 4$^{th}$ Ed., S.S. Block, ed., pp. 137-138 and 149-151, (Philadelphia, PA, Lea & Febiger, 1991).

T. Kristoffersen and I.A. Gould, "Effect of Sodium Bromide on the Bactericidal Effectiveness of Hypochlorite Sanitizers of High Alkalinity,", Journal of Dairy Science (1958) 41: 950-955.

G.U Houghton, "Bromide Content of Underground Waters. Part II. Observations on the Chlorination of Water Containing Free Ammonia and Naturally Occurring Bromide", Journal of the Society of the Chemical Industry (1946) 65: 324-328.

H. Farkas-Himsley, "Killing of Chlorine-Resistant Bacteria by Chlorine-Bromine Solutions," Applied Microbiology (1964) 12: 1-6.

P.W. Kabler, "Relative Resistance of Coliform Organisms and Enteric Pathogens in the Disinfection of Water with Chlorine," J. American Water Works Association (1951) 43: 553-560.

J.K. Johannesson, "The Bromination of Swimming Pools," American Journal of Public Health (1960) 50: 1731-1736.

J.D. Johnson and W. Sun, "Bromine Disinfection of Wastewater," in "Disinfection-Water and Wastewater," J.D. Johnson, ed., pp. 179-191 (Ann Arbor, MI: Ann Arbor Science, 1975).

J.K. Johannesson, "Anomalous Bactericidal Action of Bromamine," Nature (1958) 181: 1799-1800.

J.C. Albright, "Liquid Bromine Removes Obstinate Algae from 10,000 gpm Tower for $2.10 a Day," Petroleum Processing (1948) 3: 421-422.

Y. Kott, "Effect of Halogens on Algae-III. Field Experiment," Water Research, Pergamon Press, (1969) vol. 3, pp. 265-271.

N. Betzer and Y. Kott, "Effect of Halogens on Algae-II. *Cladophora sp.*," Water Research (1969) 3: 257-264.

Y. Kott and J. Edlis, "Effect of Halogens on Algae-I. *Chlorella sorokiniana*," Water Research (1969) 3: 251-256.

"Evolution of Industrial Water Treatment," Betz Handbook of Industrial Water Conditioning, Seventh Edition, pp. 7-15 (Trevose, PA: Betz Laboratories, Inc., 1976).

P.J. Sullivan and B.J. Hepburn, "The Evolution of Phosphonate Technology for Corrosion Inhibition," paper 496 (Houston, TX: NACE International, 1995), pp. 496/1-496/13.

W.A. Brungs, "Effects of Residual Chlorine on Aquatic Life," Journal of the Water Pollution Control Federation (1973) 45: 2180-2193.

A.T. Palin, "The Determination of Free and Combined Chlorine in Water by the Use of Diethyl-p-phenylene Diamine," Journal of the American Water Works Association (1957) 49: 873-880.

C.W. Kruse, et al., "Halogen Action on Bacteria, Viruses, and Protozoa," in Proc. Natl. Specialty Conference on Disinfection, pp. 113-136 (New York, NY: ASCE, 1970).

R. Aull and T. Krell, "Design Features and their Affect on High Performance Fill," paper TP00-01 (Houston, TX: Cooling Technology Institute, 2000), pp. 1-31.

A.E. Gillam and R.A. Morton, "The Absorption Spectra of Halogens and Inter-Halogen Compounds in Solution in Carbon Tetrachloride," Proceedings of the Royal Society (London) Series A; (1929) vol. 124: 604-616.

S. Barratt and C.P. Stein, "On Bromine Chloride," Proceedings of the Royal Society (London) Series A; (1929) vol. 122: 582-588.

J.F. Mills, "Interhalogens- and Halogen Mixtures as Disinfectants," in Disinfection-Water and Wastewater, J.D. Johnson, ed., pp. 113-143 (Ann Arbor, MI: Ann Arbor Science, 1975).

E.C. Wackenhuth and G. Levine, "An Investigation of Bromine Chloride as a Biocide in Condenser Cooling Water," (Pittsburgh, PA: Engineer's Society of Western Pennsylvania, 1974), pp. 1-14.

L.H. Bongers, T.P. O'Connor and D.T. Burton, "Bromine Chloride—An Alternative to Chlorine for Fouling Control in Condenser Cooling Systems," report No. EPA-600/7-77-053 (Research Triangle Park, NC: EPA Office of Research and Development, May 1977), 4 pages.

B.H. Keswick, "Bromine-Chloride as an Alternative Disinfectant to Chlorine of Human Enteric Viruses and Other Pathogens in Water and Wastewater", Doctoral Dissertation, University of Hawaii (Ann Arbor, MI: University Microfilms International, 1979), 16 pages.

R.M. Moore, et al., "Use of a New Bromine-Based Biocide in a Medium-Sized Cooling Tower," paper IWC-97-51 (Pittsburgh, PA: Engineers' Society of Western Pennsylvania, 1997), 6 pages.

G.D. Nelson, "Chloramines and Bromamines," Kirk-Othmer Encyclopedia of Chemical Technology, vol. 5, pp. 565-580 (New York, NY: John Wiley and Sons, 1979).

Z. Zhang and J.V. Matson, "Organic Halogen Stabilizers: Mechanisms and Disinfection Efficiencies," paper TP89-05 (Houston TX: Cooling Tower Institute, 1989), pp. 1-19.

J.C. Peterson, "Practical Air Washer Treatment in Synthetic Fiber Manufacturing Plants," paper IWC-87-39 (Pittsburgh, PA: Engineers' Society of Western Pennsylvania, 1987), pp. 366-370.

D. Vanderpool, M. Killoran, and R. Sergent, "Improving the Corrosion Inhibitor Efficiency of Tolyltriazole in the Presence of Chlorine and Bromine," paper 157 (Corrosion 87, San Francisco, CA , 1987), pp. 157/1-157/9.

C. Spurrell and J.S. Clavin, "Solid Halogen Donor Economically Answers the Challenge of SARA Title III and Corrosion Concerns," paper 474 (Corrosion 93, NACE Annual Conference and Corrosion Show, 1993), pp. 474/1-474/15.

A. Smith, et al., "Bromine vs. Gaseous Chlorine: A Comprehensive Review of Case Histories," paper 637 (Corrosion 93, NACE Annual Conference and Corrosion Show, 1993), pp. 637/1-637/12.

D.S. Larson, et al., "Improved Microbiological Control Using Halogen-Donors in a Pasteurizer," MBAA Technical Quarterly (1993) 30: 173-178.

P. Sweeney, M. Ludensky, and O. Barokhov, "Mill Performance of a Brominated Methylethylhydantoin Slimicide," pp. 437-447, Proceedings of the 1999 TAPPI Papermakers Conference (Norcross, GA:: TAPPI, 1999).

F.J. Himpler, P.G. Sweeney, and M.L. Ludensky, "The Benefits of a Hydantoin-Based Slimicide in Papermaking Applications," APPITA Journal (Sep. 2001) 54: 427-430.

M. Lewin and M. Avarahami, "The Decomposition of Hypochlorite-Hypobromite Mixtures in the pH Range 7-10," Journal of the American Chemical Society, (1955) 77: 4491-4498.

Z. Zhang, "Disinfection Efficiency and Mechanisms of 1-Bromo-3-Chloro-5,5-Dimethylhydantoin," Doctoral Dissertation, University of Houston, May 1988, pp. 160, 162, 163.

J.C. Conley, E.H. Puzig, and J.E. Alleman, "Bromine Chemistry—An Alternative to Dechlorination in Cooling Water and Wastewater Disinfection," IWC-87-42 (Pittsburgh, PA: Engineers' Society of Western Pennsylvania, 1987), pp. 389-395.

R.M. Moore, W.C. Lotz, and V.R. Perry, "Activated Sodium Bromide-Artificial Marsh Treatment: A Successful Plant-Wide Program," paper IWC-95-61 (Pittsburgh, PA: Engineers' Society of Western Pennsylvania, 1995). 12 pgs.

C.J. Nalepa, et al., "Case Study: Minimization of Corrosion Using Activated Sodium Bromide in a Medium-Size Cooling Tower," paper 485 (Corrosion 96 NACE International Annual Conference and Exposition, Houston, TX: NACE International, 1996), 485/1-485/12.

(56) References Cited

OTHER PUBLICATIONS

F.P. Yu, et al., "Cooling Tower Fill Fouling Control in a Geothermal Power Plant," paper 529 (Corrosion 98, Houston, TX: NACE International, 1998), pg. 529/1-529-11.

F.P. Yu, et al., "Innovations in Fill Fouling Control," IWC-00-03 (Pittsburgh, PA: Engineers' Society of Western Pennsylvania, 2000), pp. 26-31.

T.C. Kuechler, et al., "Development of Monsanto's Towerbrom® Microbiocide, A New Bromine Microbiocide for Recirculating Water Systems," (McLean, VA: Association of Water Technologies, 1991), 1991 AWT Conference, p. 1-23.

T.C. Kuechler, A Towerbrom® Progress Report, (McLean, VA: Association of Water Technologies, 1993 AWT Conference), pp. 1-15.

W.F. McCoy, et al., "Strategies Used in Nature for Microbial Fouling Control: Applications for Industrial Water Treatment," Paper No. 520 (Houston, TX: NACE International, 1998).

C.J. Nalepa, J.N. Howarth, and R.M. Moore, "A New, Single-Feed, Liquid Bromine Biocide for Treatment of Cooling Water," Presented at the AWT 1999 Annual Convention & Exposition, (McLean, VA: Association of Water Technologies, 1999), 17 pages.

J. Howarth et al., "First Field Trials of Single-Feed, Liquid Bromine Biocide for Cooling Towers", Paper TP00-09 (Houston, TX.: Cooling Technology Institute, Jan. 31-Feb. 2, 2000), 17 pages.

M. Enzien and B. Yang, "On-line Performance Monitoring of Treatment Programs for MIC Control," paper 01279 (Corrosion 2001, Houston, TX: NACE International, 2001), 13 pages.

Howarth, J.N., et al. "A New, Bromine-Releasing Solid for Microbiological Control of Cooling Water", IWC-01-05, (Pittsburgh, PA: Engineers' Society of Western Pennsylvania, 2001), pp. 1-7.

B.R. Sook, T.F. Ling, and A.D. Harrison "A New Thixotropic Form of Bromochlorodimethylhydantoin: A Case Study," Paper No. 03715 (Corrosion 2003, Houston, TX: NACE International, 2003), pp. 1-16.

C.J. Nalepa, et al., "Strategies for Effective Control of Surface-Associated Microorganisms: A Literature Perspective," IWC-02-01 (Pittsburgh, PA: Engineers' Society of Western Pennsylvania, 2002), 19 pages.

W.G. Characklis and K.C. Marshall, ed., Biofilms: A Basis for an Interdisciplinary Approach, (New York, NY: John Wiley & Sons, 1987), p. 3-5.

J.W. Costerton and P.S. Stewart, "Battling Biofilms," Scientific American (Jul. 2001) 285: 75-81.

M.L. Ludyanskiy and F.J. Himpler, "The Effect of Halogenated Hydantoins on Biofilms," Paper No. 405 (Corrosion 97, Houston, TX: NACE International, 1997), pp. 405/1-405/11.

L. McNamee, "Efficacy of Hypochlorite vs. Hypobromite in the Removal of a *Pseudomonas aeruginosa* Biofilm," summer intern report (Bozeman, MT: Montana State University, Center for Biofilm Engineering, 2000). pp. 1-23.

C.J. Nalepa, H. Ceri, and C.A. Stremick, "A Novel Technique for Evaluating the Activity of Biocides Against Biofilm Bacteria," Paper 00347 (Corrosion 2000, Houston, TX: NACE International, 2000), pp. 00347/1-00347/19.

W.M. Thomas, J. Eccles, and C. Fricker, "Laboratory Observations of Biocide Efficiency against *Legionella* in Model Cooling Tower Systems," paper SE-99-3-4 (Atlanta, GA: ASHRAE Transactions, 1999), pp. 1-17.

"*Legionella* 2003: An Update and Statement by the Association of Water Technologies," (McLean, VA: Association of Water Technologies, 2003). pp. 1-33.

"Minimizing the Risk of Legionellosis Associated with Building Water Systems," ASHRAE Guideline Dec. 2000 (Atlanta, GA: ASHRAE, 2000), 19 pages.

"Legionellosis Guideline: Best Practices for Control of *Legionella*," (Houston, TX: Cooling Tower Institute, Feb. 2000), 8 pages.

Guidelines for the Control of Legionnaires' Disease, (Melbourne, Australia: Health Department Victoria, 1989, (reprinted in 1999), 9 pages.

"Control of *Legionella* in Cooling Towers: Summary Guidelines," (Madison, WI: Wisconsin Division of Health, Aug. 1987), 28 pages.

M.R. Freije, "Legionellae Control in Health Care Facilities: A Guide for Minimizing Risk," (Indianapolis, IN: HC Information Resources, Inc., 1996, pp. 25-41.

E. McCall, J.E. Stout, V.L. Yu, and R. Vidic, "Efficacy of Biocides against Biofilm-Associated *Legionella* in a Model System," paper IWC 99-19 (Pittsburgh, PA: Engineers' Society of Western Pennsylvania, 1999), 7 pages.

C.J. Nalepa, et al., "The Activity of Oxidizing Biocides towards *Legionella pneumophila* and the Impact of Biofilms on its Control," paper 01278 (Houston, TX: NACE International, 2001, 21 pages.

C.J. Nalepa, et al., "The Control of Bacteria on Surfaces: Effectiveness of Bromine-Based Biocides towards Microbial Biofilms and Biofilm-Associated *Legionella pneumophila*," paper TP02-13 (Houston, TX: Cooling Technology Institute, 2002), 22 pages.

C.J. Nalepa, et al., "Case Study: A Comparison of Bromine-Based Biocides in a Medium-Size Cooling Tower," paper TP98-09 (Houston, TX: Cooling Tower Institute, 1998), 22 pages.

R. Elsmore, "Development of Bromine Chemistry in Controlling Microbial Growth in Water Systems," International Biodeterioration and Biodegradation (1994) 245-253.

C.J. Nalepa, J.N. Howarth, and F.D. Azamia, "Factors to Consider when Applying Oxidizing Biocides in the Field," paper 02223 (Houston, TX: NACE International, 2002), 20 pages.

Ault et al., "Infrared and Raman Spectra of the M+Cl3-ion Pairs and Their Chlorine—Bromine Counterparts Isolated in Argon Matrices", Journal of Chemical Physics, 1976, vol. 64, No. 12, pp. 4853-4859.

Willard, et al., "Elementary Quantitative Analysis", Third Edition, New York , D. Van Nostrand Co, Inc., Chapter XIV, 1933, pp. 261-271.

Expert Declaration of Dr. Shunong Yang, filed in Interference No. 105,230 (involving U.S. 6,287,473); this document is believed to have been made public on Sep. 29, 2005 (date of judgement in Interference No. 105,230).

* cited by examiner

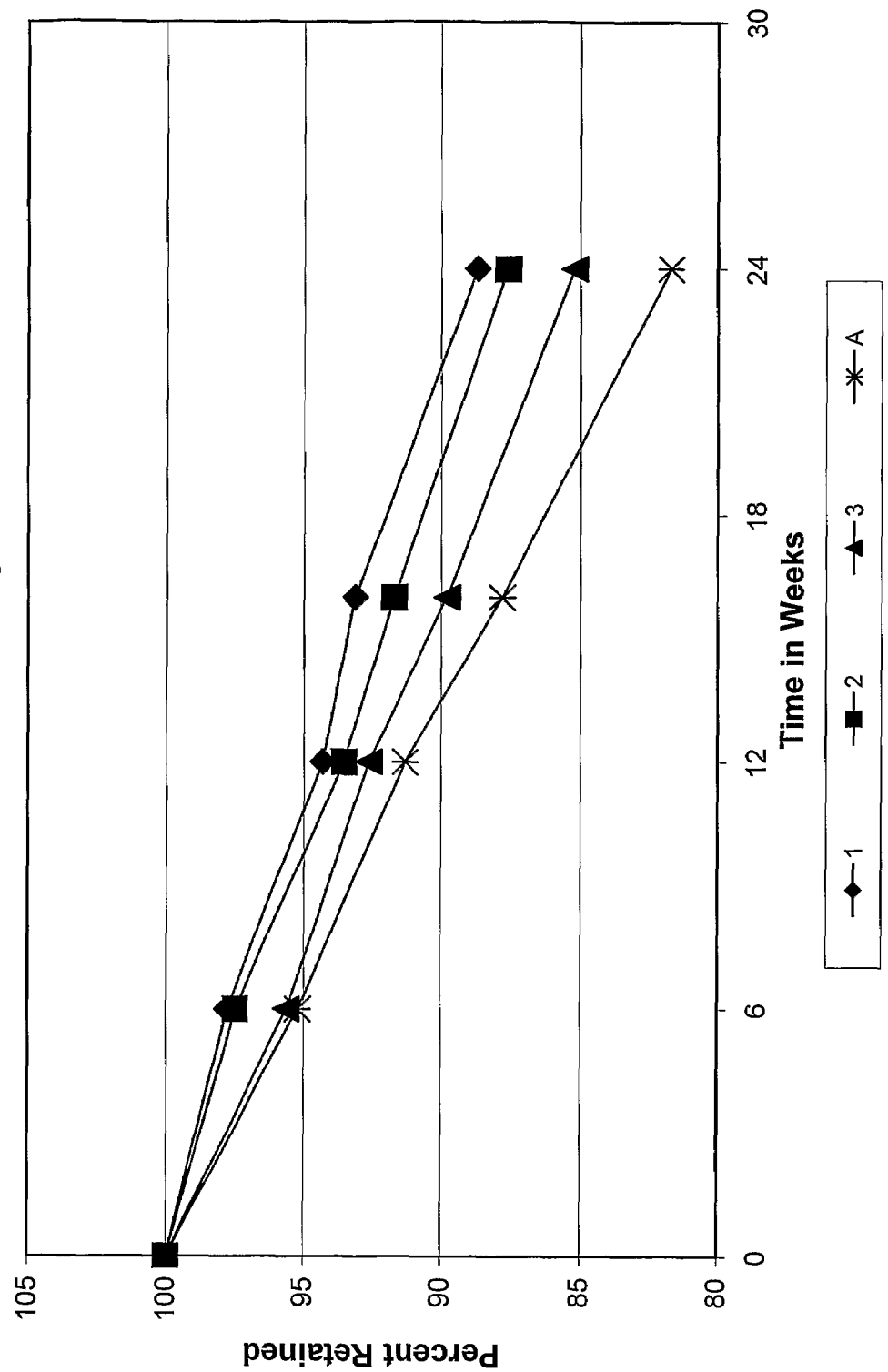

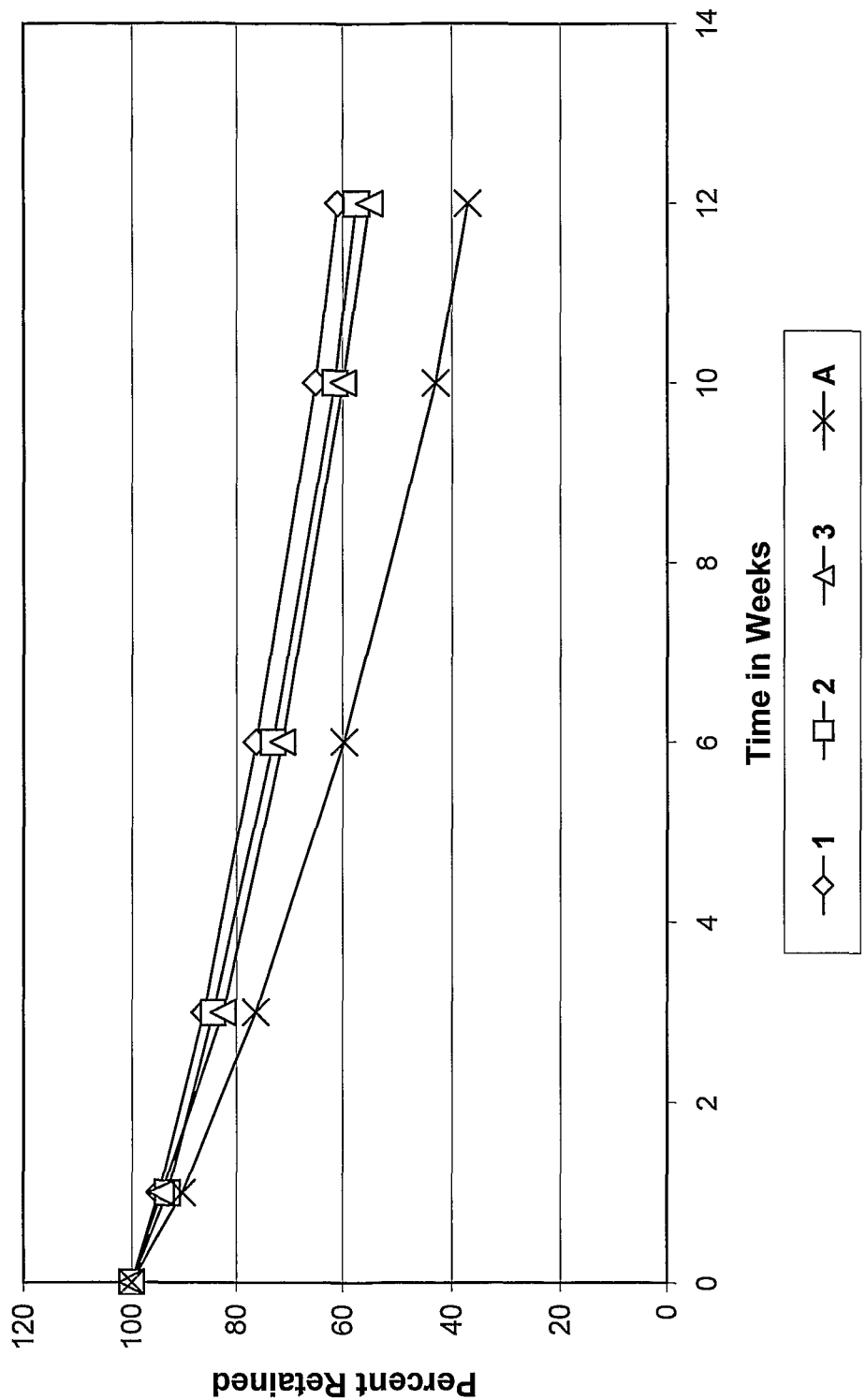

CONCENTRATED AQUEOUS BROMINE SOLUTIONS AND THEIR PREPARATION

REFERENCE TO RELATED APPLICATION

This application claims the benefit and priority of U.S. Provisional Application No. 60/607,293, filed Sep. 7, 2004, the disclosure of which is incorporated herein by reference, and is the National Stage of International Patent Appl. No. PCT/US2005/32239 filed on Sep. 7, 2005, the disclosure of which is incorporated herein by reference.

REFERENCE TO OTHER COMMONLY-OWNED APPLICATIONS

Reference is hereby made to the following commonly-owned applications: application Ser. No. 09/088,300, filed 1 Jun. 1998, now U.S. Pat. No. 6,068,861, issued 30 May 2000; application Ser. No. 09/663,948, filed 18 Sep. 2000, now U.S. Pat. No. 6,299,909, issued 9 Oct. 2001; application Ser. No. 09/442,025, filed 17 Nov. 1999, now U.S. Pat. No. 6,306,441, issued 23 Oct. 2001; application Ser. No. 09/404,184, filed 24 Sep. 1999, now U.S. Pat. No. 6,322,822, issued 27 Nov. 2001; application Ser. No. 09/663,788, filed 18 Sep. 2000, now U.S. Pat. No. 6,348,219, issued 19 Feb. 2002; application Ser. No. 09/451,344, filed 30 Nov. 1999, now U.S. Pat. No. 6,352,725, issued 5 Mar. 2002; application Ser. No. 09/456,781, filed 8 Dec. 1999, now U.S. Pat. No. 6,495,169, issued 17 Dec. 2002; application Ser. No. 09/732,601, filed 7 Dec. 2000, now U.S. Pat. No. 6,506,418, issued 14 Jan. 2003; application Ser. No. 09/506,911, filed 18 Feb. 2000, now U.S. Pat. No. 6,511,682, issued 28 Jan. 2003; application Ser. No. 09/974,622, filed 9 Oct. 2001, now U.S. Pat. No. 6,652,889, issued 25 Nov. 2003; application Ser. No. 10/269,901, filed 10 Oct. 2002, now U.S. Pat. No. 7,195,782, issued 27 Mar. 2007; application Ser. No. 10/282,291, filed 28 Oct. 2002, now U.S. Pat. No. 7,087,251, issued 8 Aug. 2006; application Ser. No. 10/282,290, filed 28 Oct. 2002, published as U.S. 2004/0022874 on 5 Feb. 2004; application Ser. No. 10/703,311, filed 7 Nov. 2003, published as U.S. 2005/0147696 on 7 Jul. 2005, now abandoned. The disclosures of the above U.S. patents and published U.S. patent applications are incorporated herein by reference as if fully set forth herein.

BACKGROUND

Bromine-based biocides have proven biocidal advantages over chlorination-dechlorination for the microbiological control of cooling waters and disinfection of waste treatment systems. The water treatment industry recognizes these advantages to include: cost-effective control at higher pH values; almost no loss in biocidal activity in the presence of ammonia; and effective control of bacteria, algae and mollusks.

A common way of introducing bromine based biocides into a water system is through the use of aqueous NaBr in conjunction with NaOCl bleach. The user feeds both materials to a common point, whereupon the NaOCl oxidizes the bromide ion to $HOBr/OBr^{\ominus}$. This activated solution is then introduced directly into the water system to be treated. The feeding of the two liquids in this fashion is necessary because the $HOBr/OBr^{\ominus}$ mixture is unstable and has to be generated on-site just prior to its introduction to the water. Furthermore, the feeding and metering of two liquids is cumbersome, especially as the system has to be designed to allow time for the activation of bromide ion to occur. Consequently, many biocide users have expressed the need for a single-feed bromine-based biocide. Elemental bromine and molecular bromine chloride have been considered to meet these demands. Both are liquids at room temperature and can be fed directly to the water system, where immediate hydrolysis occurs to yield HOBr according to the equations below.

$$Br_2 + H_2O \rightarrow HOBr + HBr \quad (1)$$

$$BrCl + H_2O \rightarrow HOBr + HCl \quad (2)$$

Certain characteristics of bromine and bromine chloride—especially their corrosiveness, high vapor pressures, and fuming tendencies—necessitate care and skill in their handling and use. Early efforts to overcome the deficiencies of these materials comprised complexing bromine with excess bromide ion in the presence of strong acid and stabilizing the resultant solutions with ethanolamine. The resultant solutions of ethanolammonium hydrogen perbromide contained up to 38% by weight elemental bromine. See in this connection: Favstritsky, U.S. Pat. No. 4,886,915; and Favstritsky, Hein, and Squires, U.S. Pat. No. 4,966,716.

These solutions permitted introduction of bromine to a water system using a single feed. As in the case of bromine and bromine chloride, the ethanolammonium hydrogen perbromide hydrolyzed in water to release HOBr. The vapor pressures of these solutions were lower than elemental bromine and bromine chloride. Nevertheless, the solutions still possessed measurable vapor pressures, and thus tended to produce undesirable reddish-colored vapors during storage and use.

Many solid bromine derivatives such as BCDMH (1,3-bromochloro-5,5-dimethylhydantoin) are limited in the amount of material that can be dissolved in water and fed as a liquid to the water treatment system. For example, the solubility of BCDMH in water is only around 0.15%. Another limitation of such derivatives is that at neutral pH, HOBr rapidly decomposes, eventually forming bromide ions. Thus, the ability to store and transport these aqueous solutions is greatly limited and of questionable commercial feasibility.

U.S. Pat. No. 3,558,503 to Goodenough et al. describes certain aqueous bromine solutions stabilized with various stabilizing agents and various uses to which such solutions can be put. The compositions described in the patent comprise an aqueous bromine solution having from about 0.01 to about 100,000 parts per million by weight of bromine values wherein the molar ratio of bromine to nitrogen present in the bromine stabilizer ranges from about 2.0 to 1 to about 0.5 to 1. The stabilizer used is biuret, succinimide, urea, a lower aliphatic mono- or disubstituted urea containing from about 2 to about 4 carbon atoms in each substituent group, sulfamic acid, or an alkyl sulfonamide of the formula $RSO_3NH_2$ where R is a methyl or ethyl group. The solution also contains sufficient hydroxide additive to provide a pH in the solution ranging from about 8 to about 10, the hydroxide additive being an alkaline earth hydroxide or an alkali metal hydroxide.

U.S. Pat. No. 5,683,654 to Dallmier et al. discusses the preparation of aqueous alkali metal or alkaline earth metal hypobromite solutions by mixing an aqueous solution of alkali or alkaline earth metal hypochlorite with a water soluble bromide ion source to form a solution of unstabilized alkali or alkaline earth metal hypochlorite. To this solution is added an aqueous solution of an alkali metal sulfamate having a temperature of at least 50° C. and in an amount that provides a molar ratio of alkali metal sulfamate to alkali or alkaline earth metal hypobromite of from about 0.5 to about 6 whereby a stabilized aqueous alkali or alkaline earth metal hypobromite solution is formed. The Dallmier et al. patent teaches that much higher levels of available halogen for disinfection were attained by this approach as compared to the Goodenough et al. approach. But the Dallmier et al. patent acknowledges that in their process, the stabilization must occur quickly after the unstable NaOBr is formed.

New process technology for forming concentrated aqueous solutions of biocidally active bromine—and, in so doing, providing novel and eminently useful concentrated aqueous biocidal solutions formed from bromine chloride—are set forth in commonly-owned U.S. Pat. Nos. 6,068,861; 6,299,909; 6,306,441; 6,322,822; 6,348,219; 6,352,725; 6,495,169; 6,506,418; and 6,511,682, and published U.S. Pat. App. Nos. 2003/0104074; 2003/0113383; 2004/0022874; and 2005/0147696, all disclosures of which are incorporated herein by reference.

SUMMARY OF THE INVENTION

It has now been found that by careful control of the relative proportions of bromine chloride, sodium hydroxide, and sulfamic acid used in forming the concentrated aqueous biocidal solutions of the foregoing commonly-owned patents, product stability—which is very good—can be more consistent. Thus, this invention provides concentrated aqueous active bromine-containing biocidal solutions that possess a more consistent, superior stability.

This invention provides novel and eminently useful concentrated aqueous biocidal solutions formed from bromine chloride, sodium hydroxide, and sulfamic acid wherein the weight ratio of bromine chloride:sodium hydroxide:sulfamic acid used in forming the concentrated solutions is such that for every 10.5 to 11.5 parts by weight of bromine chloride used, 15.3 to 17.5 parts by weight of sodium hydroxide and 11.0 to 12.5 parts by weight of sulfamic acid are used. The concentration of active bromine in the concentrated aqueous biocidal solution made from these components in these relative proportions can vary as long as the finished product solution contains at least about 100,000 ppm (wt/wt) of active bromine based on the total weight of the solution. In order to achieve the more consistent stability mentioned above, the weight ratio of bromine chloride:sodium hydroxide:sulfamic acid used in forming the concentrated solutions is such that for every 10.5 to 11.5 parts by weight of bromine chloride used, 15.3 to 16.9 parts by weight of sodium hydroxide and 11.3 to 12.5 parts by weight of sulfamic acid are used. Biocidal solutions pursuant to this invention can be produced economically and straightforwardly from relatively inexpensive raw materials and, because of their effectiveness, such biocidal solutions can provide biocidal control on an economical basis. Also provided by this invention are processes for forming the concentrated aqueous active bromine containing biocidal solutions of this invention.

An embodiment of this invention is a concentrated aqueous biocidal solution formed from bromine chloride, sodium hydroxide, and sulfamic acid. The weight ratio of bromine chloride:sodium hydroxide:sulfamic acid used in forming the concentrated solution is such that for every 10.5 to 11.5 parts by weight of bromine chloride used, 15.3 to 17.5 parts by weight of sodium hydroxide and 11.0 to 12.5 parts by weight of sulfamic acid are used. The resultant concentrated aqueous biocidal solution contains at least about 100,000 ppm (wt/wt) of active bromine based on the total weight of the solution.

Another embodiment of this invention is a concentrated aqueous biocidal solution formed from water to which has been added:

A) bromine chloride in an amount equivalent to a concentration of bromine chloride that is about 105,000 to about 115,000 ppm (wt/wt);
B) sodium hydroxide in an amount equivalent to a concentration of sodium hydroxide that is about 153,000 to about 175,000 ppm (wt/wt); and
C) sulfamic acid in an amount equivalent to a concentration of sulfamic acid that is about 110,000 to about 125,000 ppm (wt/wt).

The concentrations of A), B), and C) are each based on the total amount of A), B), C), and water used in forming the concentrated aqueous biocidal solution.

Still another embodiment of this invention is process of forming a concentrated aqueous biocidal solution. The process comprises mixing together in any subcombination(s) and in any sequence:

a) bromine chloride in an amount equivalent to a concentration of bromine chloride that is about 105,000 to about 115,000 ppm (wt/wt);
b) sodium hydroxide in an amount equivalent to a concentration of sodium hydroxide that is about 153,000 to about 175,000 ppm (wt/wt);
c) sulfamic acid in an amount equivalent to a concentration of sulfamic acid that is about 110,000 to about 125,000 ppm (wt/wt); and
d) water.

The concentrations of a), b), and c) are each based on the total amount of a), b), c), and water used in forming the concentrated aqueous biocidal solution.

The above and other embodiments of this invention will be still further apparent from the ensuing description and appended claims.

BRIEF DESCRIPTION OF THE DRAWINGS

FIG. 1 is a graph comparing the thermal stability at 104° F. of concentrated aqueous biocidal solutions of the invention with a biocidal solution in which the ratios of weight ratio of bromine chloride:sodium hydroxide:sulfamic acid used in forming the biocidal solutions is outside that of the present invention.

FIG. 2 is a graph comparing the thermal stability at 130° F. of concentrated aqueous biocidal solutions of the invention with a biocidal solution in which the ratios of weight ratio of bromine chloride:sodium hydroxide:sulfamic acid used in forming the biocidal solutions is outside that of the present invention.

FURTHER DETAILED DESCRIPTION OF THE INVENTION

Any method of the foregoing commonly-owned patents can be used in producing these new concentrated aqueous biocidal solutions, provided the bromine chloride, sodium hydroxide, and sulfamic acid are used in the relative proportions given in the preceding summary of the invention, and the quantities relative to the amount of water used in preparing the concentrated solution are such that the finished product solution contains at least 100,000 ppm (wt/wt) of active bromine on a weight basis, based on the total weight of the solution. These finished product solutions of this invention may contain as much as, say, about 145,000 to about 160,000 ppm (wt/wt) of active bromine based on the total weight of the solution. Indeed, finished product solutions having as much as about 180,000 ppm (wt/wt) or more of active bromine (based on the total weight of the solution) can be formed and provided pursuant to this invention.

Unless specifically stated otherwise herein, ppm means parts per million (wt/wt), based on the total weight of the solution. In this connection, there is a relationship between parts per million (wt/wt) and weight percent. For example, 100,000 ppm (wt/wt) is usually considered to be equivalent to 10 wt %.

Bromine chloride is usually formed from bromine and chlorine. In each of the compositions of the invention, the bromine chloride used is believed to be an equilibrium mixture. Thus, if the bromine and chlorine are mixed in molar proportions other than 1:1, the bromine chloride is believed to also contain the halogen used in excess. Preferably, equimolar amounts of bromine and chlorine or a slight excess of bromine is used in forming the bromine chloride used in the practice of this invention.

In order to employ bromine chloride most efficiently when forming the concentrated aqueous biocidal solutions of the invention, the bromine chloride is fed in the form of a liquid under pressure and typically under such conditions that the equilibrium mixture actually contains about 85 mole percent of bromine chloride, about 7.5 mole percent of bromine, and about 7.5 mole percent of chlorine. Thus, the proportions given herein relative to bromine chloride are based on use of such a liquid equilibrium mixture. In this same connection, the proportions given herein for sulfamic acid and for sodium hydroxide are for materials as if they are in the solid state and of commercial purity.

Pursuant to this invention, the weight ratio of bromine chloride:sodium hydroxide:sulfamic acid is calculated based on the combined weight of these three components only. Other substances (such as water) used to form the solution are excluded from this ratio calculation. For example, even though the sodium hydroxide may be fed as an aqueous solution, only the weight of the sodium hydroxide itself is used in the calculation. When calculating the weight ratio of bromine chloride:sodium hydroxide:sulfamic acid, the combined weight of the bromine and chlorine used in forming the bromine chloride is used for calculating the ratio, even though it is understood that not all of the bromine chloride may be in the form of bromine chloride, as discussed above.

The term "active bromine" of course refers to all bromine-containing species that are capable of biocidal activity. It is generally accepted in the art that all of the bromine in the +1 oxidation state is biocidally active and is thus included in the term "active bromine." As is well known in the art, bromine chloride has bromine in the +1 oxidation state. Thus, bromine chloride—as well as other such species, to the extent they are present—constitutes the active bromine content of the solutions of this invention. See, for example, U.S. Pat. No. 4,382,799 and U.S. Pat. No. 5,679,239. A well-established method in the art for determining the amount of active bromine in a solution is starch-iodine titration, which determines all of the active bromine in a sample regardless of what species may constitute the active bromine. The usefulness and accuracy of the classical starch-iodine method for quantitative determination of bromine and many other oxidizing agents has long been known, as witness Chapter XIV of Willard-Furman, *Elementary Quantitative Analysis*, Third Edition, D. Van Nostrand Company, Inc., New York, Copyright 1933, 1935, 1940.

A typical starch-iodine titration to determine active bromine is carried out as follows. A magnetic stirrer and 50 milliliters (mL) of glacial acetic acid are placed in an iodine flask. The sample (usually about 0.2-0.5 g) for which the active bromine is to be determined is weighed and added to the flask containing the acetic acid. Water (50 mL) and aqueous potassium iodide (15% (wt/wt); 25 mL) are then added to the flask. The flask is stoppered using a water seal. The solution is then stirred for fifteen minutes, after which the flask is unstoppered and the stopper and seal area are rinsed into the flask with water. An automatic buret (Metrohm Limited) is filled with 0.1 normal (N) sodium thiosulfate. The solution in the iodine flask is titrated with the 0.1 N sodium thiosulfate; when a faint yellow color is observed, one mL of a 1 wt % starch solution in water is added, changing the color of the solution in the flask from faint yellow to blue. Titration with sodium thiosulfate continues until the blue color disappears. The amount of active bromine is calculated using the weight of the sample and the volume of sodium thiosulfate solution titrated. Thus, the amount of active bromine in a composition of this invention, regardless of actual chemical form, can be quantitatively determined.

In one embodiment, the concentrated aqueous biocidal solutions of this invention are formed from bromine chloride, sodium hydroxide, and sulfamic acid. Water is also used in forming the concentrated aqueous biocidal solution. The amounts of bromine chloride, sodium hydroxide, and sulfamic acid used to form the concentrated solution are in a weight ratio of bromine chloride:sodium hydroxide:sulfamic acid such that for every 10.5 to 11.5 parts by weight of bromine chloride used, 15.3 to 17.5 parts by weight of sodium hydroxide and 11.0 to 12.5 parts by weight of sulfamic acid are used. The concentrated aqueous biocidal solution formed from bromine chloride, sodium hydroxide, and sulfamic acid in the given ratio has a concentration of bromine chloride that is high enough that the concentrated aqueous biocidal solution contains at least about 100,000 ppm (wt/wt) of active bromine based on the total weight of the solution. Preferably, the concentrated aqueous biocidal solution is such that for every 10.5 to 11.5 parts by weight of bromine chloride used, 15.3 to 16.9 parts by weight of sodium hydroxide and 11.3 to 12.5 parts by weight of sulfamic acid are used to form the concentrated aqueous biocidal solution; in these preferred ranges, the more consistent stability described above can be achieved.

In a more preferred embodiment, the concentrated aqueous biocidal solution of this invention is such that for every 10.8 to 11.2 parts by weight of bromine chloride used, 16.1 to 16.8 parts by weight of sodium hydroxide and 11.6 to 11.9 parts by weight of sulfamic acid are used to form the concentrated aqueous biocidal solution. Nominally, such proportions are about 11.0 parts by weight of bromine chloride, about 16.1 parts by weight of sodium hydroxide, and about 11.9 parts by weight of sulfamic acid. These more preferred proportions also allow the achievement of more consistent stability for the formed concentrated aqueous biocidal solutions.

In another embodiment, a concentrated aqueous biocidal solution of this invention is formed from water to which has been added:

A) bromine chloride in an amount equivalent to a concentration of bromine chloride that is about 105,000 to about 115,000 ppm (wt/wt);

B) sodium hydroxide in an amount equivalent to a concentration of sodium hydroxide that is about 153,000 to about 175,000 ppm (wt/wt); and C) sulfamic acid in an amount equivalent to a concentration of sulfamic acid that is about 110,000 to about 125,000 ppm (wt/wt).

The concentrations of A), B), and C) are each based on the total amount of A), B), C), and water used in forming the concentrated aqueous biocidal solution. The phrase "in an amount equivalent to a concentration of" means that the amounts of bromine chloride, sodium hydroxide, and sulfamic acid added to form the concentrated aqueous biocidal solution are such that the amount added would give a concentration in the recited range. Preferably, in order to achieve the more consistent stability referred to above, the sodium hydroxide is added in an amount to make a concentration in the solution of about 153,000 to about 169,000 ppm (wt/wt); in the preferred ranges, the more consistent stability described above can be achieved.

In more preferred embodiments, the concentrated aqueous biocidal solutions of this invention are formed from water to which has been added:
A) about 108,000 to about 112,000 ppm (wt/wt) of bromine chloride;
B) about 161,000 to about 168,000 ppm (wt/wt) of sodium hydroxide; and
C) about 116,000 to about 119,000 ppm (wt/wt) of sulfamic acid.

These more preferred proportions also allow the achievement of more consistent stability for the formed concentrated aqueous biocidal solutions. Such concentrations provide biocidal solutions which nominally contain about 110,000 ppm of bromine chloride, about 161,000 ppm of sodium hydroxide, and about 119,000 ppm of sulfamic acid.

In any of the above embodiments, at least a portion of the sodium hydroxide can be used in the form of an aqueous solution when forming the concentrated aqueous biocidal solution.

In another embodiment, this invention provides a process of forming a concentrated aqueous biocidal solution. The process comprises mixing together in any subcombination(s) and in any sequence:
a) bromine chloride in an amount equivalent to a concentration of bromine chloride that is about 105,000 to about 115,000 ppm (wt/wt);
b) sodium hydroxide in an amount equivalent to a concentration of sodium hydroxide that is about 153,000 to about 175,000 ppm (wt/wt);
c) sulfamic acid in an amount equivalent to a concentration of sulfamic acid that is about 110,000 to about 125,000 ppm (wt/wt); and
d) water.

The concentrations of a), b), and c) are each based on the total amount of a), b), c), and water used in forming the concentrated aqueous biocidal solution. The phrase "in an amount equivalent to a concentration of" means that the amounts of bromine chloride, sodium hydroxide, and sulfamic acid mixed together to form the concentrated aqueous biocidal solution are such that the amount mixed would give a concentration in the recited range. Preferably, the concentrated aqueous biocidal solution formed by mixing together bromine chloride, sodium hydroxide, sulfamic acid, and water contains at least about 100,000 ppm (wt/wt) of active bromine. More preferably, the concentrated aqueous biocidal solution contains about 145,000 to about 160,000 ppm (wt/wt) of active bromine.

In a preferred embodiment, the process of forming a concentrated aqueous biocidal solution comprises mixing together in any subcombination(s) and in any sequence:
a) bromine chloride in an amount equivalent to a concentration of bromine chloride that is about 105,000 to about 115,000 ppm (wt/wt);
b) sodium hydroxide in an amount equivalent to a concentration of sodium hydroxide that is about 153,000 to about 169,000 ppm (wt/wt);
c) sulfamic acid in an amount equivalent to a concentration of sulfamic acid that is about 113,000 to about 125,000 ppm (wt/wt); and
d) water.

In these preferred ranges, the more consistent stability described above can be achieved.

In a more preferred embodiment, the process of forming a concentrated aqueous biocidal solution comprises mixing together in any subcombination(s) and in any sequence:
a) bromine chloride in an amount equivalent to a concentration of bromine chloride that is about 108,000 to about 112,000 ppm (wt/wt);
b) sodium hydroxide in an amount equivalent to a concentration of sodium hydroxide that is about 161,000 to about 168,000 ppm (wt/wt);
c) sulfamic acid in an amount equivalent to a concentration of sulfamic acid that is about 116,000 to about 119,000 ppm (wt/wt); and
d) water.

The more preferred proportions also allow the achievement of more consistent stability for the formed concentrated aqueous biocidal solutions. Such concentrations provide biocidal solutions in which a) is nominally in an amount equivalent to a concentration of bromine chloride that is nominally about 110,000 ppm (wt/wt), b) is nominally in an amount equivalent to a concentration of sodium hydroxide of about 161,000 ppm (wt/wt), and c) is nominally in an amount equivalent to a concentration of sulfamic acid of about 119,000 ppm (wt/wt).

In a preferred embodiment, (i) the sodium hydroxide is any alkali metal hydroxide; or (ii) the sulfamic acid is an alkali metal sulfamate; or (iii) the sodium hydroxide is any alkali metal hydroxide and the sulfamic acid is an alkali metal sulfamate. More preferably, the alkali metal hydroxide is sodium hydroxide, potassium hydroxide, or both sodium hydroxide and potassium hydroxide. Even more preferred are sodium sulfamate, potassium sulfamate, or both sodium sulfamate and potassium sulfamate as the alkali metal sulfamate. A highly preferred alkali metal sulfamate is sodium sulfamate.

In all of the above embodiments, at least a portion of the water of solution may be introduced with the sodium hydroxide and/or with the sulfamic acid, and/or via a separate feed. The amounts in ppm (wt/wt) in all of the above embodiments are based on the total weight of the formed biocidal solution.

While sodium hydroxide and sulfamic acid are used preferably, in the practice of this invention equivalent amounts of other alkali metal hydroxides and equivalent amounts of alkali metal salts of sulfamic acid can be used in all of the embodiments of this invention. Mixtures of two or more alkali metal hydroxides and/or mixtures of two or more alkali metal sulfamates can be used. Mixtures of one or more alkali metal sulfamate and sulfamic acid can also be used. For simplicity, it is preferred to use one alkali metal hydroxide and it is also preferred to use sulfamic acid alone, as one alkali metal sulfamate, or as a mixture of sulfamic acid and one alkali metal sulfamate. Preferably, the alkali metal hydroxide used in the practice of this invention is sodium hydroxide and/or potassium hydroxide; more preferably, the alkali metal hydroxide is sodium hydroxide. Preferred alkali metal sulfamates are sodium sulfamate and potassium sulfamate, with sodium sulfamate being more preferred.

Optional ingredients may be included in the concentrated aqueous biocidal solutions of the invention. These optional ingredients include fragrances, stabilizers, corrosion inhibitors, dyes, other biocidal agents, surfactants, effervescents, diluents, builders, chelating agents, dispersants, and the like. Such ancillary materials should of course be compatible with the biocidal solution and not interfere in any material way with the performance characteristics of the concentrated aqueous biocidal solution.

It is to be understood that some or all of the sulfamic acid used in forming the concentrated aqueous product solutions of this invention can first be neutralized by some of the sodium hydroxide to form sodium sulfamate, which is then used along with the remainder of the sodium hydroxide in forming such concentrated aqueous biocidal solutions. In other words, the aqueous solution of alkali metal salt of sulfamic acid can be preformed by mixing together in water, (I) sulfamic acid and/or an alkali metal salt of sulfamic acid, and (II) alkali metal base in proportions such that an aqueous solution of alkali metal salt of sulfamic acid is formed, preferably having a pH of at least 12. When sulfamic acid itself is used as the starting material for forming an alkali metal sulfamate, it is used initially as a slurry in water with which the alkali metal base is mixed.

When introducing bromine chloride into an aqueous solution of alkali metal salt of sulfamic acid (preferably formed from sulfamic acid and sodium hydroxide), it is desirable to maintain the desired pH of the solution at 7 or above by also introducing into the solution (continuously or intermittently, as desired) additional alkali metal base, such as by a co-feed of an aqueous solution of alkali metal base (preferably an aqueous solution of sodium hydroxide) during the feeding of the bromine chloride. When the concentrated aqueous biocidal solution is to be stored (e.g., in drums), and especially when being stored for a prolonged length of time, it is desirable to have the pH of such solution at about 10 or above. The concentrated aqueous biocidal solutions of this invention preferably have a pH of at least about 12; more preferred is a pH in the range of about 12.5 to about 14. Still more preferably, the pH of the concentrated aqueous biocidal solutions is in the range of about 13 to about 14.

A general, non-limiting procedure for preparing the compositions of this invention using sulfamic acid involves, as a first step, forming a slurry of sulfamic acid in water. Typically the pH of this slurry is below 1 pH unit. Sodium hydroxide (at, e.g., 25 wt % or 50 wt % concentration) is then added until the solid is completely dissolved. Additional sodium hydroxide (at, e.g., 25 wt % or 50 wt % concentration) is added until the desired pH is reached. Bromine chloride is then added at a rate to allow the bromine chloride to dissolve and react with the sulfamic acid without forming a pool of halogen on the bottom of the reactor. On a laboratory scale, a convenient rate of addition is approximately two drops per second. Sodium hydroxide (e.g., 25 wt % or 50 wt %) is co-fed to the reactor to maintain the desired pH (e.g., in the range of 7 to about 13.5, and it may be possible to operate even at a pH in the range of 13.5 to 14). It has been found that stable solutions containing as much as 16 wt % active bromine as bromine chloride can be prepared by the process of this invention.

At present, a preferred way of conducting the process of this invention on a larger scale involves charging to a reactor water, aqueous alkali metal hydroxide solution (preferably aqueous sodium hydroxide solution), sulfamic acid, and then bromine chloride. Preferred proportions of the components are 12.7 parts by weight of water, 64.4 parts by weight of a 25 wt % aqueous sodium hydroxide solution, 11.9 parts by weight of sulfamic acid, and 11 parts by weight of bromine chloride, for a total of 100 parts by weight. Preferably these components are charged in the order named. However, as long as the bromine chloride is charged last, the order of addition of the other three components can be varied. The bromine chloride used preferably contains in the range of 68.9 to 73.1 wt % bromine. However, pure bromine chloride or other combinations of bromine chloride and bromine can be used to make effective product, if desired. The temperature of the mixture during the addition of the bromine chloride is preferably not allowed to exceed 50° C., although the temperature can be allowed to go above 50° C. for short periods of time without detrimental effects. Prolonged exposure to elevated temperatures tends to cause degradation of the product, and thus should be avoided. The bromine chloride concentration in the resultant product biocidal solution as formed in this manner (and in whatever chemical form or forms the active bromine chloride exists in such solution), is in the range of about 10.5 wt % to about 11.5 wt % (i.e., between about 105,000 and about 115,000 ppm (wt/wt)), and preferably is in the range of about 10.8 wt % to about 11.2 wt % (i.e., between about 108,000 to about 112,000 ppm (wt/wt)). Determination of the active bromine concentration can, of course, be readily accomplished by starch-iodine titration. When operating as described in this paragraph, the final pH of the product solution is in the range of about 12.4 to about 13.7.

Another preferred way of operating on a larger scale the process described in the immediately preceding paragraph is in a semi-continuous or semi-batch mode. This involves forming the alkali metal sulfamate solution, preferably a sodium sulfamate solution (using caustic, water, and sulfamic acid), and feeding in the bromine chloride to a suitable vessel (reactor, tank, etc.) containing the sulfamate solution. The BrCl may go straight into the vessel of the aqueous sodium sulfamate or into a pump around loop on the vessel. The BrCl may be made up ahead of time, or can be made by continuously mixing the bromine and chlorine together in a pipe, with or without a mixing element, and then injecting it straight into the aqueous sodium sulfamate without isolating the BrCl. The advantage of continuously making the BrCl is that this avoids having a separate BrCl reactor or storage tank and the need for keeping a large quantity of this material in storage on plant facilities.

The following Examples are presented for purposes of illustration and not limitation. These Examples set forth preferred procedures for preparing a biocidal concentrated aqueous biocidal solution of this invention.

EXAMPLE 1

The total quantities of the components used in forming a preferred composition of this invention are as follows: 7.81 g bromine, 3.19 g chlorine (to form bromine chloride), 32.2 g 50 wt % aqueous sodium hydroxide solution, 11.9 g sulfamic acid, and 44.9 g water. The procedure used involves charging water to the reactor, followed by separately cofeeding sulfamic acid and aqueous 50 wt % sodium hydroxide solution to the reactor while maintaining the temperature at about 70 to about 80° F. (about 21 to about 27° C.) and the pH at about 9 to about 12. Next, bromine chloride and aqueous 50% sodium hydroxide solution are separately co-fed into the reactor while maintaining the temperature below about 80° F. (about 26° C. or less) and the pH in the range of about 8 to about 12. The mixture is then held under these conditions for about 15 minutes. Then, the remainder of the aqueous 50 wt % sodium hydroxide solution is added. Typically, the pH of the resultant product solution will be greater than about 12.

EXAMPLE 2

A 500 mL round-bottom flask was charged with water (129.1 g) and sulfamic acid (112.3 g). The resultant slurry was stirred and then aqueous sodium hydroxide solution (50 wt %, 303.7 g) was slowly introduced. The flask contents were kept below 30° C. during the addition. Chlorine (31.2 g) was added to 75.9 g of bromine (to form bromine chloride), and then added to the flask. The flask contents again were kept below 30° C. during the addition. At the end of the bromine chloride addition, a slightly hazy orange solution was obtained. The solution had a BrCl:NaOH:sulfamic acid ratio of 11.0:15.6:11.5. The activity of the product solution was 15.9 wt % as bromine chloride, as determined by starch-iodine titration, corresponding to 22.0 wt % active bromine on a $Br_2$ basis.

EXAMPLE 3

A commercial-size glass-lined reactor was charged with water. Sulfamic acid and sodium hydroxide (50 wt %) were co-fed while maintaining the pH between 9 and 12. Bromine chloride and aqueous sodium hydroxide (50 wt %) were then co-fed under essentially the same conditions, followed by a final charge of aqueous sodium hydroxide (50 wt %) to make the pH of the solution greater than 12. The temperature during these operations was maintained at 80° F. (~27° C.) or less. The amounts of reagents used were such that 11.2 parts BrCl, 16.1 parts sodium hydroxide (100% solids basis), and 11.6 parts sulfamic acid had been added to the reactor. The activity of the product was 11.0 wt % as BrCl as determined by the KI/thiosulfate method. This corresponds to 15.2 wt % active bromine on a $Br_2$ basis. The pH of the product solution was 13.4.

EXAMPLE 4

A solution was prepared as described in Example 3. The amounts of reagents used were such that 11.2 parts BrCl, 16.1 parts sodium hydroxide (100% solids basis), and 11.6 parts sulfamic acid had been added to the reactor. The activity of the product was 11.1 wt % as BrCl as determined by the KI/thiosulfate method, which corresponds to 15.4 wt % active bromine on a $Br_2$ basis. The pH of the product solution was 13.5.

EXAMPLE 5

Solutions of the invention (Runs 1-3) were prepared as described in Examples 3 and 4. For comparison, a solution having 11.0 parts BrCl, ~14.75 parts sodium hydroxide, and ~13.0 parts sulfamic acid were also made (Run A; preparation of this solution was otherwise similar to that in Examples 3 and 4). To test their thermal stability, samples of these solutions were exposed to room temperature, 104° F. (40° C.), or 130° F. (54° C.) for three to six months. The results of these studies are summarized in Tables 1-3; the activities in Tables 1-3 are in weight percent, as BrCl. The activities of the solutions were determined by the KI/thiosulfate method. The column labeled "Retained" shows how much of the original activity remains after the elapsed time.

TABLE 1

(Room temperature)

| Solution | Run 1 | | Run 2 | | Run 3 | | Run A | |
|---|---|---|---|---|---|---|---|---|
| | wt % BrCl | Retained | wt % BrCl | Retained | wt % BrCl | Retained | wt % BrCl | Retained |
| Initial | 10.6 | | 11.0 | | 11.21 | | 10.57 | |
| 12 weeks | 10.63 | 100% | 11.02 | 100% | 11.20* | 99.9% | 10.6 | 100% |
| 24 weeks | 10.62 | 100% | 10.98 | 99.8% | 10.68 | 98.5% | 10.59 | 100% |

*This solution was measured after 13 weeks.

TABLE 2

(104° F.)

| Solution | Run 1 | | Run 2 | | Run 3 | | Run A | |
|---|---|---|---|---|---|---|---|---|
| | wt % BrCl | Retained | wt % BrCl | Retained | wt % BrCl | Retained | wt % BrCl | Retained |
| Initial | 10.6 | | 11.0 | | 11.21 | | 10.57 | |
| 6 weeks | 10.37 | 97.8% | 10.72 | 97.5% | 10.72 | 95.6% | 10.06 | 95.2% |
| 12 weeks | 9.99 | 94.3% | 10.28 | 93.5% | 10.38* | 92.6% | 9.65 | 91.3% |
| 16 weeks | 9.87 | 93.1% | 10.09 | 91.7% | 10.07 | 89.8% | 9.28 | 87.8% |
| 24 weeks | 9.40 | 88.7% | 9.63 | 87.6% | 9.55 | 85.2% | 8.62 | 81.7% |

*This solution was measured after 13 weeks.

TABLE 3

(130° F.)

| Solution | Run 1 | | Run 2 | | Run 3 | | Run A | |
|---|---|---|---|---|---|---|---|---|
| | wt % BrCl | Retained | wt % BrCl | Retained | wt % BrCl | Retained | wt % BrCl | Retained |
| Initial | 10.6 | | 11.0 | | 11.21 | | 10.57 | |
| 1 week | 10.04 | 94.7% | 10.24 | 93.1% | 10.56 | 94.2% | 9.54 | 90.3% |
| 3 weeks | 9.14 | 86.2% | 9.28 | 84.4% | 9.25 | 82.5% | 8.07 | 76.4% |
| 6 weeks | 8.09 | 76.3% | 8.04 | 73.1% | 7.99 | 71.3% | 6.31 | 59.7% |
| 10 weeks | 6.90 | 65.1% | 6.75 | 61.4% | 6.71 | 59.9% | 4.53 | 42.9% |
| 12 weeks | 6.45 | 60.9% | 6.33 | 57.5% | 6.18 | 55.1% | 3.91 | 37.0% |

Tables 1-3 show that although the comparative solution of Run A are stable, the solutions of the present invention (Runs 1-3) exhibit a more consistent stability over time, especially upon prolonged exposure to increased temperatures. The data regarding the percent of activity retained in Table 2 is presented graphically in FIG. 1, and the data regarding the percent of activity retained in Table 3 is presented graphically in FIG. 2. The Figures show that for both 104° F. and 130° F., while there is decay in the amount of activity in all of the solutions tested, the solutions of the invention (labeled 1, 2, and 3 in the Figures) retained a greater amount of activity over time as compared to that of the comparative solution (labeled A in the Figures).

Even though the claims hereinafter may refer to substances, components and/or ingredients in the present tense ("comprises", "is", etc.), the reference is to the substance, component or ingredient as it existed at the time just before it was first contacted, blended or mixed with one or more other substances, components and/or ingredients, or if formed in solution, as it would exist if not formed in solution, all in accordance with the present disclosure. It matters not that a substance, component or ingredient may have lost its original identity through a chemical reaction or transformation during the course of such contacting, blending, mixing, or in situ formation, if conducted in accordance with this disclosure.

Each and every patent or publication referred to in any portion of this specification is incorporated into this disclosure by reference, as if fully set forth herein.

This invention is susceptible to considerable variation in its practice. Therefore the foregoing description is not intended to limit, and should not be construed as limiting, the invention to the particular exemplifications presented hereinabove. Rather, what is intended to be covered is as set forth in the ensuing claims and the equivalents thereof permitted as a matter of law.

The invention claimed is:

1. A concentrated aqueous biocidal solution formed from bromine chloride, sodium hydroxide, and sulfamic acid wherein the weight ratio of bromine chloride:sodium hydroxide:sulfamic acid used in forming the concentrated solution is such that for every 10.5 to 11.5 parts by weight of bromine chloride used, 15.3 to 17.5 parts by weight of sodium hydroxide and 11.0 to 12.5 parts by weight of sulfamic acid are used, said biocidal solution containing 100,000 ppm (wt/wt) or more of active bromine based on the total weight of said solution.

2. A solution as in claim 1 wherein said weight ratio is such that for every 10.5 to 11.5 parts by weight of bromine chloride used, 15.3 to 16.9 parts by weight of sodium hydroxide and 11.3 to 12.5 parts by weight of sulfamic acid are used.

3. A solution as in claim 1 wherein said weight ratio is such that for every 10.8 to 11.2 parts by weight of bromine chloride used, 16.1 to 16.8 parts by weight of sodium hydroxide and 11.6 to 11.9 parts by weight of sulfamic acid are used.

4. A solution as in claim 3 wherein said weight ratio is such that for every 11.0 parts by weight of bromine chloride, 16.1 parts by weight of sodium hydroxide and 11.9 parts by weight of sulfamic acid are used.

5. A solution as in claim 4 wherein said biocidal solution has a pH of 12 or more.

6. A solution as in claim 1 wherein said biocidal solution contains in the range of 145,000 to 160,000 ppm (wt/wt) of active bromine.

7. A solution as in claim 1 wherein at least a portion of the sodium hydroxide is used in the form of an aqueous solution.

8. A solution as in claim 1 wherein said biocidal solution has a pH of 10 or more.

9. A solution as in claim 1 formed from water to which has been added:
A) bromine chloride in an amount equivalent to a concentration of bromine chloride that is 105,000 to 115,000 ppm (wt/wt);
B) sodium hydroxide in an amount equivalent to a concentration of sodium hydroxide that is 153,000 to 175,000 ppm (wt/wt); and
C) sulfamic acid in an amount equivalent to a concentration of sulfamic acid that is 110,000 to 125,000 ppm (wt/wt),
wherein the concentrations of A), B), and C) are each based on the total amount of A), B), C), and water used, and wherein said solution has a pH in the range of about 12.4 to about 13.7.

10. A solution as in claim 9 formed from water to which has been added:
A) bromine chloride in an amount equivalent to a concentration of bromine chloride that is 105,000 to 115,000 ppm (wt/wt);
B) sodium hydroxide in an amount equivalent to a concentration of sodium hydroxide that is 153,000 to 169,000 ppm (wt/wt); and
C) sulfamic acid in an amount equivalent to a concentration of sulfamic acid that is 113,000 to 125,000 ppm (wt/wt),
wherein the concentrations of A), B), and C) are each based on the total amount of A), B), C), and water used.

11. A solution as in claim 9 formed from water to which has been added:
A) bromine chloride in an amount equivalent to a concentration of bromine chloride that is 108,000 to 112,000 ppm (wt/wt);
B) sodium hydroxide in an amount equivalent to a concentration of sodium hydroxide that is 161,000 to 168,000 ppm (wt/wt); and
C) sulfamic acid in an amount equivalent to a concentration of sulfamic acid that is 116,000 to 119,000 ppm (wt/wt),
wherein the concentrations of A), B), and C) are each based on the total amount of A), B), C), and water used.

12. A solution as in claim 11 formed from water to which has been added:
A) bromine chloride in an amount equivalent to a concentration of bromine chloride that is nominally 110,000 ppm (wt/wt);
B) sodium hydroxide in an amount equivalent to a concentration of sodium hydroxide that is nominally 161,000 ppm (wt/wt); and
C) sulfamic acid in an amount equivalent to a concentration of sulfamic acid that is nominally 119,000 ppm (wt/wt),
wherein the concentrations of A), B), and C) are each based on the total amount of A), B), C), and water used.

13. A solution as in claim 1 formed from water to which has been added:
A) bromine chloride in an amount equivalent to a concentration of bromine chloride that is 105,000 to 115,000 ppm (wt/wt);
B) sodium hydroxide in an amount equivalent to a concentration of sodium hydroxide that is 153,000 to 175,000 ppm (wt/wt); and
C) sulfamic acid in an amount equivalent to a concentration of sulfamic acid that is 110,000 to 125,000 ppm (wt/wt),
wherein the concentrations of A), B), and C) are each based on the total amount of A), B), C), and water used, and wherein said solution has a pH in the range of about 12.5 to about 14.

14. A solution as in claim 13 wherein said biocidal solution has a pH in the range of about 13 to about 14.

15. A solution as in claim 9 wherein said biocidal solution has 100,000 ppm (wt/wt) or more of active bromine based on the total weight of said solution.

16. A solution as in claim 9 wherein said biocidal solution contains in the range of 145,000 to 160,000 ppm (wt/wt) of active bromine based on the total weight of said solution.

17. A concentrated aqueous biocidal solution formed from bromine chloride, at least one alkali metal hydroxide, and sulfamic acid and/or an alkali metal sulfamate wherein the weight ratio of bromine chloride:alkali metal hydroxide:sulfamic acid used in forming the concentrated solution is such that for every 10.5 to 11.5 parts by weight of bromine chloride used, 15.3 to 17.5 parts by weight of sodium hydroxide and 11.0 to 12.5 parts by weight of sulfamic acid are used, said biocidal solution containing 100,000 ppm (wt/wt) or more of active bromine based on the total weight of said solution, wherein:
 (i) an equivalent amount of at least one other alkali metal hydroxide is used in place of at least a portion of the sodium hydroxide; or
 (ii) an equivalent amount of an alkali metal sulfamate is used in place of at least a portion of the sulfamic acid; or
 (iii) an equivalent amount of at least one other alkali metal hydroxide is used in place of at least a portion of the sodium hydroxide and an equivalent amount of an alkali metal sulfamate is used in place of at least a portion of the sulfamic acid.

18. A solution as in claim 17 wherein the alkali metal hydroxide is sodium hydroxide, potassium hydroxide, or both sodium hydroxide and potassium hydroxide.

19. A solution as in claim 17 wherein the alkali metal sulfamate is sodium sulfamate, potassium sulfamate, or both sodium sulfamate and potassium sulfamate.

20. A process of forming a concentrated aqueous biocidal solution which comprises mixing together in any subcombination(s) and in any sequence:
 a) bromine chloride in an amount equivalent to a concentration of bromine chloride that is 105,000 to 115,000 ppm (wt/wt);
 b) sodium hydroxide in an amount equivalent to a concentration of sodium hydroxide that is 153,000 to 175,000 ppm (wt/wt);
 c) sulfamic acid in an amount equivalent to a concentration of sulfamic acid that is about 110,000 to 125,000 ppm (wt/wt); and
 d) water,
 wherein the concentrations of a), b), and c) are each based on the total amount of a), b), c), and water used.

21. A process as in claim 20 wherein the amount in a) is an amount equivalent to a concentration of bromine chloride that is 105,000 to 115,000 ppm (wt/wt), wherein the amount in b) is an amount equivalent to a concentration of sodium hydroxide that is 153,000 to 169,000 ppm (wt/wt), and wherein the amount in c) is an amount equivalent to a concentration of sulfamic acid that is 113,000 to 125,000 ppm (wt/wt).

22. A process as in claim 20 wherein the amount in a) is an amount equivalent to a concentration of bromine chloride that is 108,000 to 112,000 ppm (wt/wt), wherein the amount in b) is an amount equivalent to a concentration of sodium hydroxide that is 161,000 to 168,000 ppm (wt/wt), and wherein the amount in c) is an amount equivalent to a concentration of sulfamic acid that is 116,000 to 119,000 ppm (wt/wt).

23. A process as in claim 22 wherein the amount in a) is an amount equivalent to a concentration of bromine chloride that is nominally 110,000 ppm (wt/wt), wherein the amount in b) is an amount equivalent to a concentration of sodium hydroxide that is nominally 161,000 ppm (wt/wt), and wherein the amount in c) is an amount equivalent to a concentration of sulfamic acid that is nominally 119,000 ppm (wt/wt).

24. A process as in claim 20 wherein said mixing together forms a biocidal solution containing 100,000 ppm (wt/wt) or more of active bromine based on the total weight of said solution.

25. A solution as in claim 20 wherein said mixing together forms a biocidal solution containing in the range of 145,000 to 160,000 ppm (wt/wt) of active bromine based on the total weight of said solution.

26. A process of forming a concentrated aqueous biocidal solution which comprises mixing together in any subcombination(s) and in any sequence:
 a) bromine chloride in an amount equivalent to a concentration of bromine chloride that is 105,000 to 115,000 ppm (wt/wt);
 b) an alkali metal hydroxide in an amount equivalent to a concentration of sodium hydroxide that is 153,000 to 175,000 ppm (wt/wt);
 c) sulfamic acid and/or an alkali metal sulfamate in an amount equivalent to a concentration of sulfamic acid that is 110,000 to 125,000 ppm (wt/wt); and
 d) water,
 wherein the concentrations of a), b), and c) are each based on the total amount of a), b), c), and water used.

27. A process as in claim 26 wherein the alkali metal hydroxide is sodium hydroxide, potassium hydroxide, or both sodium hydroxide and potassium hydroxide.

28. A process as in claim 26 wherein the alkali metal sulfamate is sodium sulfamate, potassium sulfamate, or both sodium sulfamate and potassium sulfamate.

29. A solution as in claim 17 formed from water to which has been added:
 A) bromine chloride in an amount equivalent to a concentration of bromine chloride that is 105,000 to 115,000 ppm (wt/wt);
 B) sodium hydroxide in an amount equivalent to a concentration of sodium hydroxide that is 153,000 to 175,000 ppm (wt/wt); and
 C) sulfamic acid in an amount equivalent to a concentration of sulfamic acid that is 110,000 to 125,000 ppm (wt/wt),
 wherein:
 (i) an equivalent amount of one other alkali metal hydroxide is used in place of a portion of the sodium hydroxide; or
 (ii) an equivalent amount of an alkali metal sulfamate is used in place of at least a portion of the sulfamic acid; or
 (iii) an equivalent amount of one other alkali metal hydroxide is used in place of a portion of the sodium hydroxide and an equivalent amount of an alkali metal sulfamate is used in place of at least a portion of the sulfamic acid;
 wherein the concentrations of A), B), and C) are each based on the total amount of A), B), C), and water used.

30. A solution as in claim 29 wherein the alkali metal hydroxide is both sodium hydroxide and potassium hydroxide.

31. A solution as in claim 29 wherein the alkali metal sulfamate is sodium sulfamate, potassium sulfamate, or both sodium sulfamate and potassium sulfamate.

* * * * *